United States Patent [19]
Jones et al.

[11] Patent Number: 6,112,747
[45] Date of Patent: Sep. 5, 2000

[54] METHOD OF STERILIZING FEMALES

[76] Inventors: Jesse M. Jones, 2682 Harvest Dr., Conyers, Ga. 30013; Edward L. Sinofsky, 152 Whittier Dr., Dennis, Mass. 02638

[21] Appl. No.: 09/187,213

[22] Filed: Nov. 6, 1998

[51] Int. Cl.$^7$ ........................................................ A61F 6/06
[52] U.S. Cl. ........................................... 128/830; 128/831
[58] Field of Search ..................................... 128/830–841

[56] References Cited

U.S. PATENT DOCUMENTS

| | | | |
|---|---|---|---|
| 5,323,778 | 6/1994 | Kandarpa et al. | 128/653.2 |
| 5,382,247 | 1/1995 | Cimino et al. | 606/33 |
| 5,549,600 | 8/1996 | Cho | 606/15 |
| 5,607,420 | 3/1997 | Schuman | 606/15 |
| 5,695,493 | 12/1997 | Nakajima et al. | 606/13 |
| 5,743,900 | 4/1998 | Hara | 606/7 |
| 5,755,850 | 5/1998 | Martin et al. | 65/387 |

OTHER PUBLICATIONS

Transcervical sterilization with use of methyl 2–cyanoacrylate and a newer delivery system (the FEMCEPT device); Jack Shuber, M.D., pp. 887–889.

A multi–centre collaborative study into the treatment of menorrhagia by Nd–YAG laser ablation of the endometrium; Dr. Ray Garry, et al., pp. 357–362.

Transcervical sterilization in the human female by hysteroscopic application of hydrogelic occulusive devices into the intramural parts of the Fallopian tubes: 10 years experience of the P–block; Jan Brudin, pp. 41–49.

American Association of Gynecologic Laparoscopists' 1998 membership survey on laparoscopic sterilization; Dr. Jaroslav Hulka, et al., pp. 584–586.

Method failures of laparoscopic tubal sterilization in residency training program. A comparison of the tubal ring and spring–loaded clip; Dr. Thomas Stovall, et al., pp. 283–286.

Female sterilzations in the United States, 1987; Dana Schwartz, et al., pp. 209–212, Oct. 1989.

Attempted transcervical occulsion of the fallopian tube with the ND:YAG laser; Dr. John Brumsted, et al., pp. 327–328.

Falloposcopy: a microendoscopic technique for visual exploration of the human fallopian tube from the uterotubal ostium to the fimbria using a transvaginal approach; Dr. Kerin, et al., pp. 390–400.

*Primary Examiner*—Michael A. Brown
*Attorney, Agent, or Firm*—Kennedy, Davis & Hodge

[57] ABSTRACT

A method of sterilizing women is provided wherein a flexible hysteroscope (10), having an operating channel (11), a fluid channel (12), and an optical channel terminating at a lens (13), is passed through the cervix C and uterus to a position adjacent the utero-tubal ostium. An elongated laser catheter (15) having a radially diffusing tip (16) and coupled to a laser generator is extended from the operating channel and through the utero-tubal ostium to a position within the fallopian tube. The laser generator is then energized so as to generate energy sufficient to cause the production of oxygen free radicals which cause necrosis and ultimate fibroses of the fallopian tube.

30 Claims, 1 Drawing Sheet

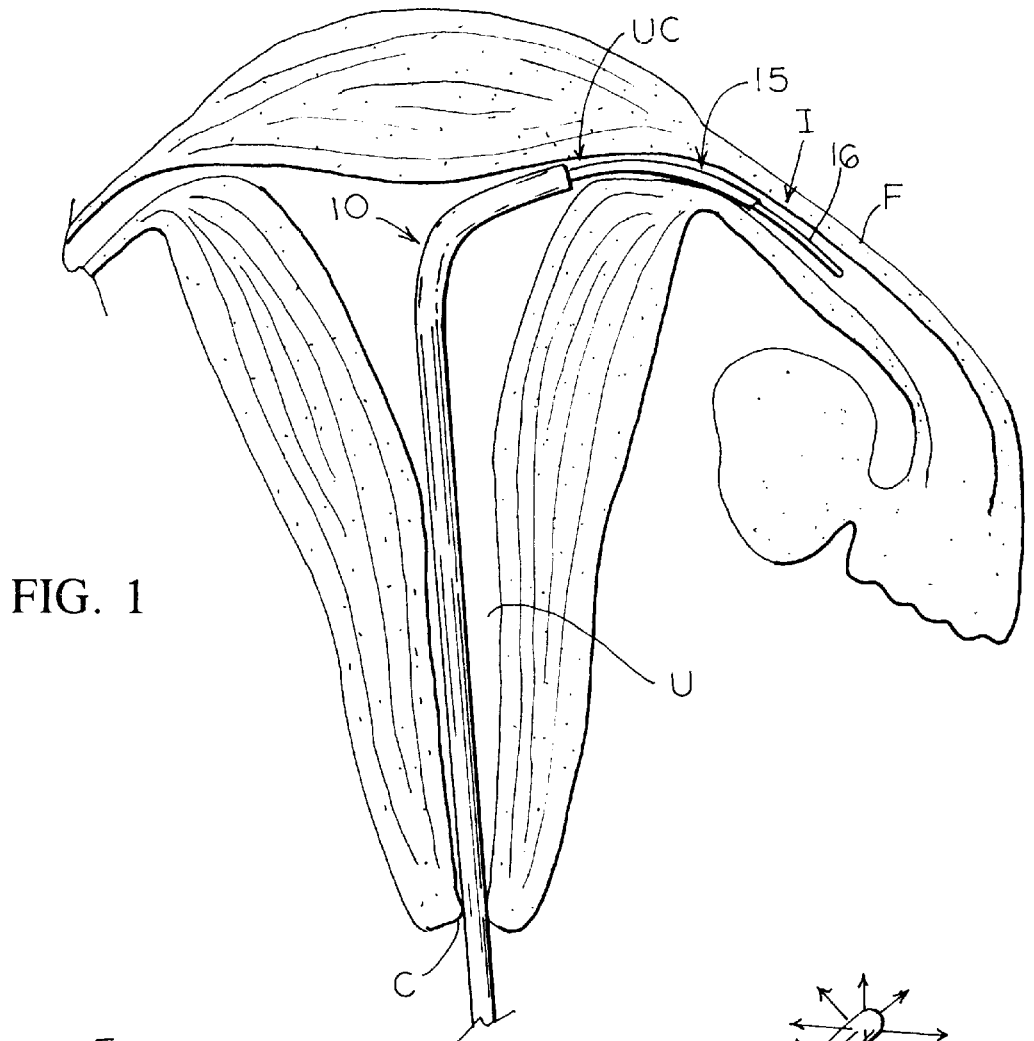
FIG. 1
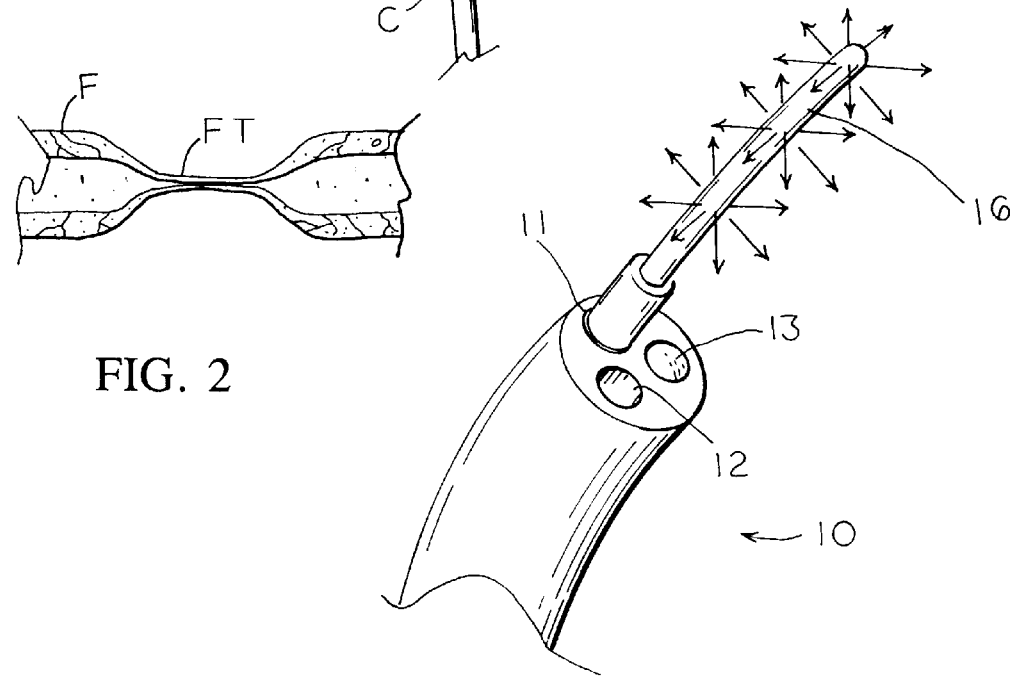
FIG. 2
FIG. 3

METHOD OF STERILIZING FEMALES

TECHNICAL FIELD

This invention relates to a method of irreversibly sterilizing females through laser radiation therapy.

BACKGROUND OF THE INVENTION

It is often necessary or desirous for a female to become sterile in order to prevent pregnancy. Tubal sterilization remains the most common method of sterilization in the world. It is estimated that this procedure is done more than 10 million times annually throughout the world.

In the past, a common method of tubal sterilization has been by tubal occlusion, which itself may be accomplished in several different manners. One manner of accomplishing this has been to position a blocking agent within the fallopian tube to prevent the passage of eggs therethrough. The blocking agent may be in the form of a glue, a plug or a coil. Another manner of accomplishing tubal occlusion has been to place chemicals within the tube which cause injury to the fallopian tube cells which in turn results in the production of scar tissue which occludes the tubes. Similarly, electrodes may be placed within, or about, the fallopian tube which causes a current to be passed between the electrodes which injure the fallopian tube cells. Lastly, occlusion may be performed by restricting the fallopian tube with an externally mounted fallopian ring.

Despite the effectiveness of laparoscopic tubal occlusion, problems associated with these procedures still exists. One problem has been the expense associated with these procedures since they require operating room facilities as well as a general or regional anesthetic. These requirements have been the principle limitation on the availability of this procedure in third-world countries and less affluent segments of our society. Another problem has been a well defined morbidity associated with this procedure, even though such is relatively low. Also, because of the complexity of the procedure, the effectiveness or success rate of the procedure is relative to the experience of the surgeon conducting the procedure.

Another method of tubal sterilization has been to surgically sever or tie off the fallopian tube. This procedure is typically accomplished by grasping the fallopian tube and pulling upon it to form a loop or sharp bend. The bent fallopian tube is either tied off and physically severed or tied off tightly to prevent the flow of blood through the bight area of the bend resulting in necrosis of the bight area. This procedure however has many of the same economic and physical limitation previously discussed, as well as being more physically invasive than the previous procedure. Furthermore, the severed tube may reconnect itself through re-anastomosis resulting in the ultimate failure of the procedure.

Another recent method of sterilization has been attempted which utilizes a laser positioned within the uterus. The laser is oriented to direct a destructive light at the utero-tubal ostium, the opening between the fallopian tube and the uterus, in an attempt to cause damage to the area of the uterus about the utero-tubal ostium. The damaged area of the uterus is intended to heal with a resulting closing of the utero-tubal ostium. This method has proven to be very unreliable because of tissue revitalization.

Accordingly, it is seen that a need remains for a method of sterilizing women in an economic and effective manner with minimum morbidity. It is to the provision of such therefore that the present invention is primarily directed.

SUMMARY OF THE INVENTION

In a preferred form of the invention a method of sterilizing a female is preformed wherein the interior of the fallopian tube is irradiated with radiation sufficient to cause the production of oxygen-free radicals within the cells sufficient to cause necrosis of a length of the fallopian tube which causes fibrosis of the length of the necrotic area.

BRIEF DESCRIPTION OF THE DRAWING

FIG. 1 is a front view of the internal organs of a female undergoing the sterilization method of the present invention.

FIG. 2 is a perspective view of the end portion of a hysteroscope and laser catheter tip utilized in the sterilization method.

FIG. 3 is a cross-section view of the treated fallopian tube of FIG. 1 shown coagulated.

DETAILED DESCRIPTION

With reference next to the drawings, there is shown a flexible hysteroscope 10, such as that made by Olympus America Inc., model number HYFXP, having an operating channel 11, a fluid channel 12, and an optical channel terminating at a lens 13, as shown best in FIG. 3. An elongated laser catheter or optical fiber 15, preferably of a 200 micrometer diameter, is reciprocally mounted within the operating channel 11 of the hysteroscope. The laser catheter 15 terminates in a 3–5 centimeter diffusing tip 16 which emits light in a 360 degree radial pattern along the axis of the tip, such as that manufactured by Rare Earth Medical, Inc of Yarmouth, Mass. and described in detail in U.S. patent Ser. Nos. 08/827,631 and 08/991,130 specifically incorporated herein. As used herein the term tip refers to the energy emitting portion of the laser fiber and not merely the endmost extreme of the laser fiber. The diffusing tip 16 preferably has a rounded end to minimize accidental piercing of tissue and a polytetrafluorethylene coating to prevent adherence to tissue. The laser catheter 15 is coupled to a conventional laser generator, preferably a 6 watt, 120 volt, diode laser with a wavelength of 980 nanometers such as a Polaroid diode Alto 6206 made by Polaroid Corp. The diode laser may be equipped with a safety interlock or shutoff circuit to sense for and react to the detect of a failure in the fiber. This may be done by the conventional detection of blackbody radiation, which if detected will automatically stop all laser activity.

To practice the inventive procedure the hysteroscope is passed through the cervical ostium C and into the uterus U, as shown in FIG. 1. With the physician viewing the path of the hysteroscope through the operating channel 11, the hysteroscope is guided up through the uterus to a position wherein the tip of the hysteroscope is adjacent the utero-tubal ostium UC. To aid visualization of the hysteroscope through the uterus a fluid, such as carbon dioxide gas, glycine, lactated Ringer's or saline solution, may be passed through the hysteroscope fluid channel 12 and into the uterus to cause it to distend. The laser catheter 15 is then extended from the hysteroscope so that the laser tip 16 is positioned within the isthmic portion I of the fallopian tube F. The laser catheter may be uniformly marked to aid the physician in determining the extent to which the laser catheter is inserted within the fallopian tube.

Once the laser tip is properly positioned, the laser generator is energized thereby passing the light energy through the laser catheter wherein it is dispersed uniformly in a generally radial manner along the length of the tip, as described in detail in U.S. patent Ser. No. 08.827,631, thereby irradiating a length of the fallopian tube. It is believed that energization of the laser generator for 5 minutes at a level of 4 watts, for a total of 1,200 joules, provides an optimal energy output level sufficient to penetrate at least a majority of the thickness of the fallopian tube walls and optimally at least two thirds of the thickness of the walls to prevent re-anastomosis and re-epithelization of the fallopian tube. The laser catheter is then withdrawn from the fallopian tube and into the hysteroscope. The hysteroscope is then manipulated so that the opposite fallopian tube is treated in like manner. Once, both fallopian tubes have been treated, the hysteroscope is withdrawn through the uterus and cervical ostium.

The exposure of the fallopian tube interior walls and liners to the light energy causes the chromophores, the pigmented material, within these cells to absorb the light energy resulting in the production of oxygen-free radicals. The production of these oxygen-free radicals produce heat within the cells, which in turn cause the irreversible binding of protein therein and thus coagulation necrosis of the fallopian tubes. This coagulation necroses is followed by edema, hemorrhage, the invasion of polymorphonuclear leukocytes (PMN's), macrophages, and eventually, fibroblasts. The final result of these physiological occurrences is that the treated areas of fallopian tubes form a thin wisp of fibrous tissues FT, as shown in FIG. 2. As such, a length of the fallopian tube is now obliterated, thereby preventing the passage of an egg through the fallopian tube.

It is believed that the 980 nanometer wavelength achieved with the 980 nm Diode laser provides the optimal results because the chromophores within the cells of the fallopian tube walls and liner absorb energy of this wavelength most efficiently, i.e. because of the interaction of this wavelength with the chromophores of the cells of the fallopian tube walls and liner and the heat produced as a result thereof. However, the present invention is not limited to the preferred embodiments as it should be understood that energy of different wavelengths, albeit less efficient, may be used in connection with the sterilization method. For example, tests on the fallopian tubes of animals have been conducted with argon lasers, KTP 532 nanometer laser such as that made by Laserscope, Inc. of San Jose, Calif., and 810 nanometer diode lasers. However, argon lasers while providing good interaction with the chromophores proved to the ergonomically problematic due to high power requirements as well as the need to dissipate the waste heat with active water cooling. These problems would make office based procedures prohibitive and field based procedures impossible. The KTP laser while causing some successful procedures provided poor overall results, believed to be associated with the adequacy of the 532 nanometer wavelength of this laser. The 810 nanometer diode laser caused damage to the cells of the fallopian tube walls and liner. However, the lack of chromophores at the 810 nanometer wavelength forced the use of higher power to obtain results similar to that of the 980 nanometer diode laser. More significantly however, the low absorption in the thin walled fallopian tube illuminates structures, such as the bowel, that surrounds the fallopian tube that are not intended to be treated. As such, it should be understood that a wavelength of between 400 and 2,200 may be utilized to carry out the sterilization method, but that a laser producing light energy at approximately a 980 nanometer wavelength is preferred so as to react well with the chromophores within the cells of the fallopian tube walls and liner.

It is also believed that a wattage of between 2 and 10 watts is required. A wattage level greater than 10 watts may cause collateral damage to adjacent structures and may cause the fallopian to burst because of the rapid vaporization of liquid within the cells of the tube. A wattage level below 2 watts would not suffice since the heat generated by the laser would be dissipated by blood flow through the tissue, resulting in a steady state heat level inadequate to cause the proper tissue damage.

Similarly, an energization time interval of between 1 minute and 10 minutes is preferred. A time interval greater than 10 minutes would unnecessarily require the patient to endure to procedure while remaining motionless. Furthermore, a prolonged time period would require a low wattage to prevent over-energization of the fallopian tube. This prolong time period may be such that the generated heat may be dissipated by the body prior to achieving the proper cellular damage, as previously described. Conversely, an energization time interval less than 1 minute would require a large corresponding wattage and the dangers associated therewith, as previously described.

Furthermore, it is believed that the laser tip should be at least 2 centimeters in length to insure that a sufficient length of the fallopian tube is damaged to prevent re-anastomosis and re-epithelization of the tube, Also, it is believed that the tip should not be longer than 5 centimeters in length, as a tip of a greater length would be difficult to control within the fallopian tube and the even distribution of energy from the tip would be difficult to achieve.

With the proceeding correlation of the desired wavelengths, wattages and time intervals, it should be understood that an energy level of between 60 joules and 3000 joules is preferred, and an energy level of 1,200 joules dispersed by a 5 centimeter tip is believed to be optimal.

It should be understood that the procedure may be accomplished with other types of flexible or rigid fiber optic scopes.

While this invention has been described in detail with particular references to the preferred embodiment thereof, it should be understood that many modifications, additions and deletions, in addition to those expressly recited, may be made thereto without departure from the spirit and scope of the invention as set forth in the following claims.

We claim:

1. A method of sterilizing a female wherein the interior of the fallopian tube is irradiated with radiation sufficient to cause the production of oxygen-free radicals within the cells sufficient to cause necrosis of a length of the fallopian tube which causes fibrosis of the length of the necrotic area.

2. The method of claim 1 wherein the fallopian tube is irradiated with radiation having an energy level of between 2 and 10 watts.

3. The method of claim 2 wherein the fallopian tube is irradiated with radiation having a wavelength of between 400 nanometers and 2,200 nanometers.

4. The method of claim 3 wherein the fallopian tube is irradiated with between 60 and 3,000 joules of radiation.

5. The method of claim 4 wherein the fallopian tube is irradiated with approximately 1,200 joules of radiation.

6. The method of claim 1 wherein the fallopian tube is irradiated with radiation having a wavelength of between 400 nanometers and 2,200 nanometers.

7. The method of claim 1 wherein the radiation is provided by a laser fiber passed through the cervix and into the fallopian tube through the utero-tubal ostium.

8. The method of claim 1 wherein the radiation is emitted radially from the laser tip.

9. The method of claim 8 wherein the radiation is emitted radially from the laser tip in a generally 360 degree radial pattern.

10. The method of claim 9 wherein the tip emits a substantially 360 degree radial pattern of light exposure along an elongated portion of the tip.

11. The method of claim 10 wherein the tip radiates energy along a length of between 2 centimeters and 5 centimeters of the fallopian tube.

12. A method of sterilizing a female wherein the fallopian tube is irradiated with laser generated energy of a frequency, power and time period sufficient to cause the production of oxygen-free radicals within at least a majority of the thickness of a portion of the fallopian tube to cause necrosis of a portion of the fallopian tube.

13. The method of claim 12 wherein the fallopian tube is irradiated with radiation having an energy level of between 2 watts and 10 watts.

14. The method of claim 13 wherein the fallopian tube is irradiated with radiation having a wavelength of between 400 nanometers and 2,200 nanometers.

15. The method of claim 12 wherein the fallopian tube is irradiated with radiation having a wavelength of between 400 nanometers and 2,200 nanometers.

16. The method of claim 12 wherein the radiation is provided by a laser fiber passed through the cervix and into the fallopian tube through the utero-tubal ostium.

17. The method of claim 12 wherein the radiation is emitted radially from the laser tip.

18. The method of claim 17 wherein the radiation is emitted from the laser tip along a substantially 360 degree radial pattern.

19. The method of claim 18 wherein the tip emits a substantially 360 degree radial pattern of light exposure along an elongated portion of the tip.

20. The method of claim 19 wherein between 2 centimeters and 5 centimeters of the fallopian tube is irradiated.

21. A method of human female sterilization comprising the steps of:

(a) providing a fiber optic scope operable coupled with a laser having an elongated optic fiber with a sideways emitting tip;

(b) passing the fiber optic scope through the cervix to a position adjacent the utero-tubal ostium;

(c) extending the laser tip into the fallopian tube;

(d) energizing the laser causing the emission of light from the laser tip;

(e) maintaining the energization of the laser for a select time interval to cause thermal damage to the fallopian tube adjacent the laser tip;

(f) withdrawing the laser tip from the fallopian tube; and (g) withdrawing the fiber optic scope through the cervix.

22. The method of claim 21 wherein the laser tip emits light along an elongated portion of the laser tip.

23. The method of claim 22 wherein light is emitted from the elongated portion along a length of between 2 centimeters and 5 centimeters.

24. The method of claim 21 wherein the laser tip emits a substantially 360 degree radial pattern of light exposure along.

25. The method of claim 24 wherein the laser tip emits a substantially 360 degree radial pattern of light exposure along an elongated portion of the laser tip.

26. The method of claim 25 wherein light is emitted from the elongated portion along a length of between 2 centimeters and 5 centimeters.

27. The method of claim 21 wherein the provided laser is a diode laser.

28. The method of claim 27 wherein the light emitted from the laser has a wavelength of between 400 nanometers and 2,200 nanometers.

29. The method of claim 21 wherein the laser tip is positioned within the isthmic portion of the fallopian tube.

30. The method of claim 21 wherein the fallopian tube is exposed to between 60 and 3,000 joules of light energy.

* * * * *